(12) United States Patent
Meehan et al.

(10) Patent No.: US 11,633,116 B2
(45) Date of Patent: Apr. 25, 2023

(54) SYSTEM AND METHOD FOR INTERFERENCE AND MOTION DETECTION FROM DARK PERIODS

(71) Applicant: Covidien LP, Mansfield, MA (US)

(72) Inventors: Christopher Meehan, Denver, CO (US); Robert Eikel, Lafayette, CO (US); Daniel Lisogurski, Boulder, CO (US); Eric Morland, Erie, CO (US)

(73) Assignee: COVIDIEN LP, Mansfield, MA (US)

( * ) Notice: Subject to any disclaimer, the term of this patent is extended or adjusted under 35 U.S.C. 154(b) by 311 days.

(21) Appl. No.: 16/859,066

(22) Filed: Apr. 27, 2020

(65) Prior Publication Data

US 2021/0330208 A1 Oct. 28, 2021

(51) Int. Cl.
*A61B 5/1455* (2006.01)
*A61B 5/024* (2006.01)
*A61B 5/00* (2006.01)

(52) U.S. Cl.
CPC ...... *A61B 5/02427* (2013.01); *A61B 5/02416* (2013.01); *A61B 5/14551* (2013.01); *A61B 5/7207* (2013.01); *A61B 5/7225* (2013.01)

(58) Field of Classification Search
CPC .............. A61B 5/1455; A61B 5/14551; A61B 5/02416; A61B 5/7207; A61B 5/7225
See application file for complete search history.

(56) References Cited

U.S. PATENT DOCUMENTS

| | | |
|---|---|---|
| 9,220,409 B2 | 12/2015 | Lisogurski |
| 10,188,330 B1 | 1/2019 | Kadlec et al. |
| 2016/0206247 A1 | 7/2016 | Morland et al. |
| 2018/0344255 A1 | 12/2018 | Orron et al. |

OTHER PUBLICATIONS

International Application No. PCT/US2021/028759 International Search Report and Written Opinion dated Jul. 30, 2021, 10 pages.

*Primary Examiner* — Eric F Winakur
(74) *Attorney, Agent, or Firm* — Cantor Colburn LLP (57) ABSTRACT

Systems and methods for interference and motion detection from dark periods are provided, including analysis of a physiological signal to determine a physiological parameter of a subject, using a photoplethysmography system to monitor signals during an LED-off period to identify interference or motion artifacts in the signal.

16 Claims, 5 Drawing Sheets

SYSTEM AND METHOD FOR INTERFERENCE AND MOTION DETECTION FROM DARK PERIODS

FIELD

The present technology is generally related to processing physiological signals. More particularly, the present technology relates to processing photoplethysmography signals, comprising light signals attenuated by a subject, including signals during a dark period.

BACKGROUND

One practice in processing physiological signals, in general, and photoplethysmography signals in particular, relates to the presence and handling of noise from various sources present in the detected signal. Such noise can be from a variety of sources, including external interference, such as overhead LED lighting, EMI, surgical equipment, motion effects, line noise, etc.

One practice is the use of a high pass filter to remove the DC content of a dark period to improve detection of the signal during the light period. While this approach can be effective to strip away noise to improve detection during the light period, there is room in the field for further improvement.

SUMMARY

The techniques of this disclosure generally relate to systems and methods of processing a physiological signal to determine a physiological parameter of a subject, using a photoplethysmography system, such as a pulse oximeter, to monitor signals during an LED-off period to identify interference or motion artifacts in the signal.

In one aspect, the present disclosure provides that the LED-off period is unfiltered by high pass filtering to preserve signal details for interference or motion detection.

In another aspect, the disclosure provides for removal of detected interference and/or motion from the light-on signal.

In another aspect, the disclosure provides for the generation of an alert upon detection of interference and/or motion.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure is directed to processing physiological signals received from one or more sensors coupled to a subject. The physiological signals may be used by a physiological monitor to determine one or more physiological parameters of the subject. The sensors may include a light source for emitting light which may pass through perfused tissue of the subject. After the light has passed through the tissue of the subject it may be received by a detector. The detector may provide a signal proportional to the intensity of the received light. In some embodiments, the physiological signal provided by the detector may be representative of physiological information about the blood of the subject since light of different wavelengths passing through tissue may be differentially absorbed depending on, for example, oxygen saturation of the blood. The physiological monitor may analyze the physiological signal to determine one or more physiological parameters such as pulse rate, respiration rate, and oxygen saturation.

In some embodiments, the sensor includes a photoplethysmography system. In additional exemplary embodiments, the sensor is part of a pulse oximetry system. In further exemplary embodiments the sensor is part of a regional saturation monitors with plural light emitters.

In exemplary embodiments, light drive circuitry generates a light drive signal, which may be used to turn on and off the light source, based on the timing control signals. That light drive signal may also include dark periods, which are periods during which no drive current are applied to light source. Dark periods may be provided, for example, to prevent overlap of the emitted light, since the light source may require time to turn completely on and completely off. In exemplary aspects described herein, rather than filtering out the signal during the dark period, the detected signal is analyzed to evaluate motion (which may include triboelectric effects, among other motion) and/or external interference. In additional exemplary embodiments, high pass filtering of the DC content of the dark period is not performed; and the DC portion of the dark period is permitted to pass through to also be represented in the detected signal.

In exemplary embodiments, detection continues during a dark period, with a determination of percent modulation in the dark period to determine a motion signal. In further exemplary embodiments, such dark period motion signal is used to remove motion and/or to warn the system that motion is present (for example as an indicator to ignore non-dark period measurements).

In further exemplary embodiments, the signal detected during the dark period is analyzed to detect external interference (which may otherwise look like a pulse), for example from overhead LED lighting, EMI, surgical equipment, etc. In further exemplary embodiments, such dark period external interference signal is used to remove external interference and/or to warn the system that external interference is present (for example as an indicator to ignore non-dark period measurements).

Figure 1:
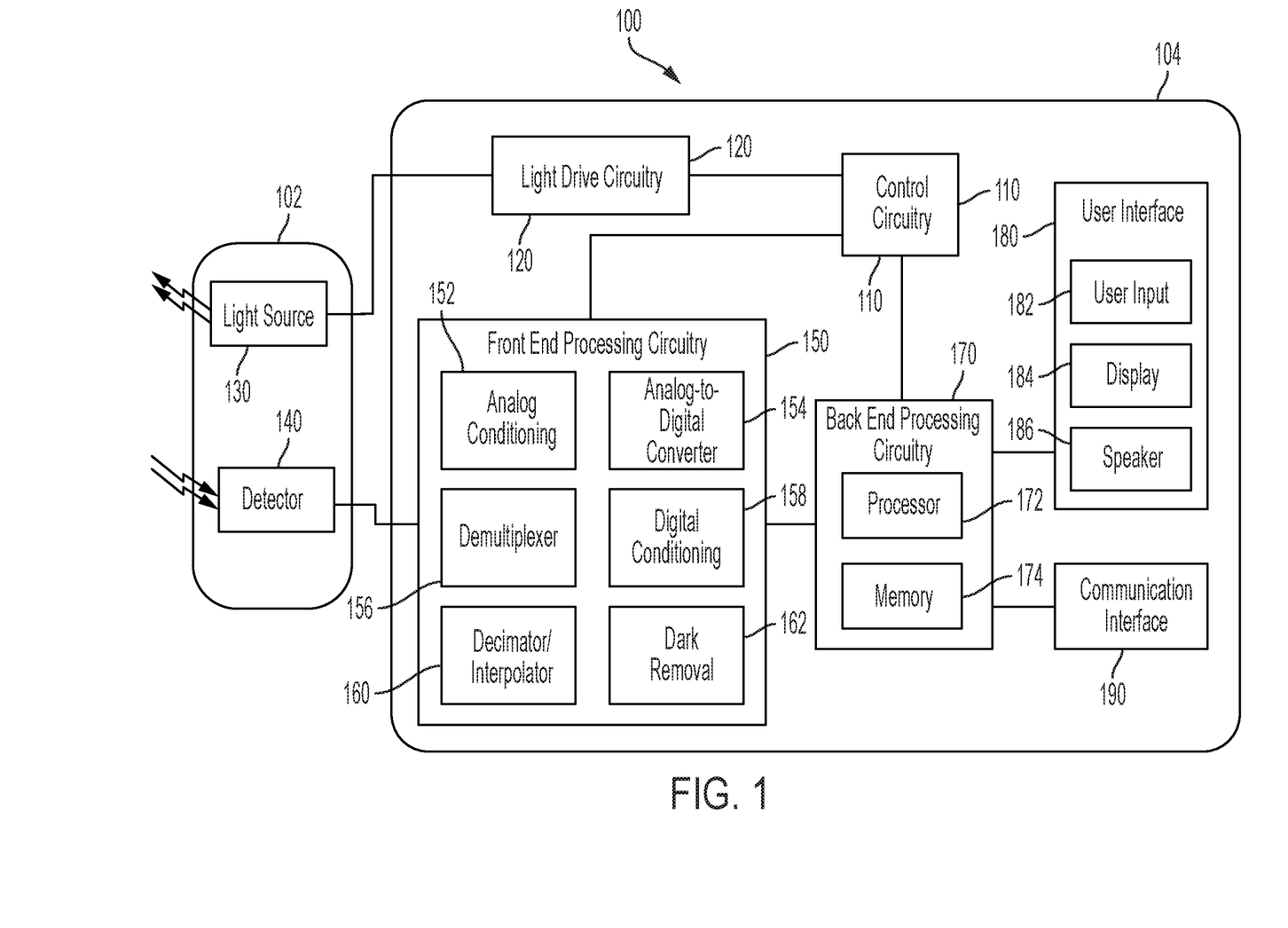
FIG. 1 is a block diagram of an illustrative physiological monitoring system in accordance with some embodiments of the present disclosure.

FIG. 1 is a block diagram of an illustrative physiological monitoring system 100 in accordance with some embodiments of the present disclosure. System 100 may include a sensor 102 and a monitor 104 for generating and processing physiological signals of a subject. In some embodiments, sensor 102 and monitor 104 may be part of an oximeter.

Sensor 102 of physiological monitoring system 100 may include light source 130 and detector 140. Light source 130 may be configured to emit photonic signals having one or more wavelengths of light (e.g. Red and IR) into a subject's tissue. For example, light source 130 may include a Red light emitting light source and an IR light emitting light source, e.g. Red and IR light emitting diodes (LEDs), for emitting light into the tissue of a subject to generate physiological signals. In one embodiment, the Red wavelength may be between about 600 nm and about 700 nm, and the IR wavelength may be between about 800 nm and about 1000 nm. In embodiments where an array of sensors is used in place of single sensor 102, each sensor may be configured to emit a single wavelength. For example, a first sensor may emit only a Red light while a second may emit only an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 140 may be chosen to be specifically sensitive to the chosen targeted energy spectrum of light source 130. Detector 140 may be chosen to also be sensitive to ambient light sources.

In some embodiments, detector 140 may be configured to detect the intensity of light at the Red and IR wavelengths. In some embodiments, an array of sensors may be used and each sensor in the array may be configured to detect an intensity of a single wavelength. In operation, light may enter detector 140 after passing through the subject's tissue. Detector 140 may convert the intensity of the received light into an electrical signal. The light intensity may be directly related to the absorbance and/or reflectance of light in the tissue. That is, when more light at a certain wavelength is absorbed or reflected, less light of that wavelength is received from the tissue by detector 140. After converting the received light to an electrical signal, detector 140 may send the detection signal to monitor 104, where the detection signal may be processed and physiological parameters may be determined (e.g., based on the absorption of the Red and IR wavelengths in the subject's tissue). In some embodiments, the detection signal may be preprocessed by sensor 102 before being transmitted to monitor 104.

In the embodiment shown, monitor 104 includes control circuitry 110, light drive circuitry 120, front end processing circuitry 150, back end processing circuitry 170, user interface 180, and communication interface 190. Monitor 104 may be communicatively coupled to sensor 102.

Control circuitry 110 may be coupled to light drive circuitry 120, front end processing circuitry 150, and back end processing circuitry 170, and may be configured to control the operation of these components. In some embodiments, control circuitry 110 may be configured to provide timing control signals to coordinate their operation. For example, light drive circuitry 120 may generate a light drive signal, which may be used to turn on and off the light source 130, based on the timing control signals. The front end processing circuitry 150 may use the timing control signals to operate synchronously with light drive circuitry 120. For example, front end processing circuitry 150 may synchronize the operation of an analog-to-digital converter and a demultiplexer with the light drive signal based on the timing control signals. In addition, the back end processing circuitry 170 may use the timing control signals to coordinate its operation with front end processing circuitry 150.

Light drive circuitry 110, as discussed above, may be configured to generate a light drive signal that is provided to light source 130 of sensor 102. The light drive signal may, for example, control the intensity of light source 130 and the timing of when light source 130 is turned on and off. When light source 130 is configured to emit two or more wavelengths of light, the light drive signal may be configured to control the operation of each wavelength of light. The light drive signal may comprise a single signal or may comprise multiple signals (e.g., one signal for each wavelength of light). An illustrative light drive signal is shown in FIG. 2A.

Figure 2A:
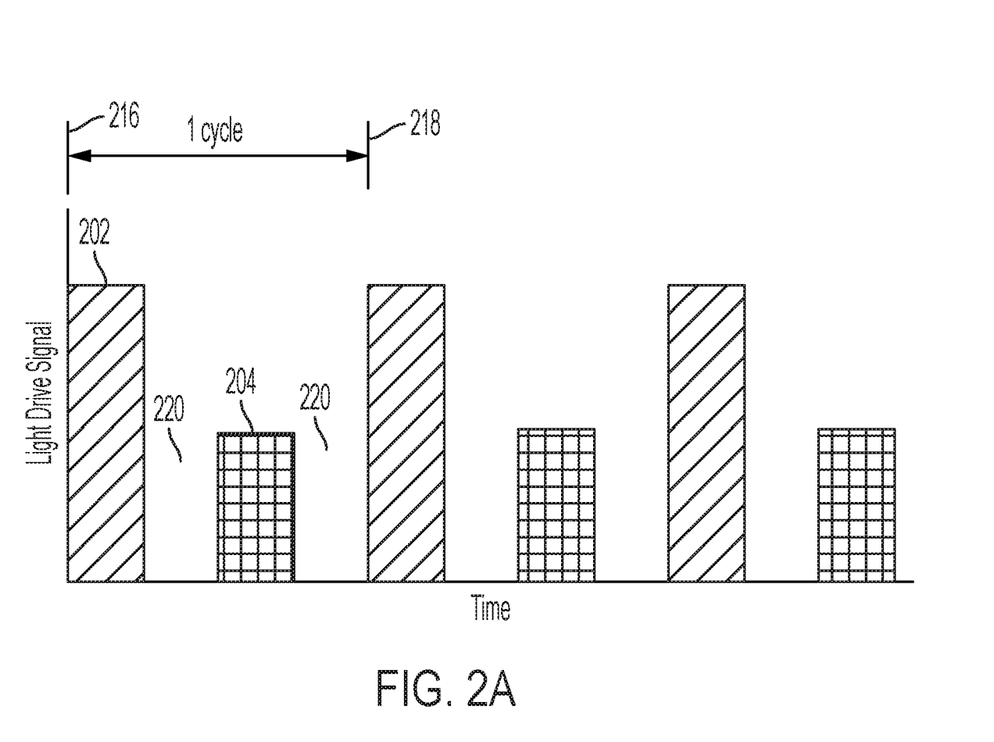
FIG. 2A shows an illustrative plot of a light drive signal in accordance with some embodiments of the present disclosure.

FIG. 2A shows an illustrative plot of a light drive signal comprising Red light drive pulse 202 and IR light drive pulse 204 in accordance with some embodiments of the present disclosure. Light drive pulses 202 and 204 may be generated by light drive circuitry 120 under the control of control circuitry 110. The light drive signal may be provided to light source 130 and Red light drive pulse 202 and IR light drive pulse 204 may be used to drive Red and IR light emitters, respectively, within light source 130. Red light drive pulse 202 may have a different amplitude than IR light drive pulse 204 since Red and IR light have different absorption in tissue depending on oxygenation levels. Additionally, the LEDs may have different efficiencies in converting current to light and the photodetector transfer function of light to electrical current may also depend on the wavelength of light. When the Red and IR light sources are driven in this manner they emit pulses of light at their respective wavelengths into the tissue of a subject in order generate physiological signals that physiological monitoring system 100 may process to calculate physiological parameters.

The light drive signal of FIG. 2A may also include dark periods 220 between the Red and IR light drive pulses. Dark periods 220 are periods during which no drive current may be applied to light source 130. Dark periods 220 may be provided, for example, to prevent overlap of the emitted light, since light source 130 may require time to turn completely on and completely off. The period from time 216 to time 218 may be referred to as a drive cycle, which includes four segments: a Red light drive pulse 202, followed by a dark period 220, followed by an IR light drive pulse 204, and followed by a dark period 220. After time 218 the drive cycle may be repeated (e.g., as long as a light drive signal is provided to light source 130). It will be understood that the starting point of the drive cycle is merely illustrative and that the drive cycle can start at any location within FIG. 2A, provided the cycle spans two light drive pulses and two dark periods. Thus, each Red light drive pulse 202 and each IR light drive pulse 204 may be understood to be surrounded by two dark periods 220.

It will be understood that the light drive signal shown in FIG. 2A is merely illustrative and that any other suitable light drive schemes may be used. For example, in some embodiments, the drive cycle may include three segments instead of four, where one of the dark periods shown in FIG. 2A is eliminated. As another example, while FIG. 2A illustrates a time-division multiplexing scheme for the Red and IR light emitters, other multiplexing schemes may be used such as frequency division multiplexing (e.g., where the emitters are modulated at different frequencies), CDMA multiplexing, any other suitable type of multiplexing, or any combination thereof.

Additionally, other modulation techniques include frequency division multiplexing or phase multiplexing, gathering of a motion signal using a frequency separation with low pass and high pass filters, etc. In exemplary embodiments, the motion signal modulates the DC light sources so frequency content is in a frequency band, e.g., from 0 to 10 Hertz, with LED signals at a higher rate (e.g, double side band modulated from the carrier, e.g., 1211 Hz+/−10 Hz).

Referring back to FIG. 1, front end processing circuitry 150 may receive a detection signal from detector 140 and provide one or more processed signals to back end processing circuitry 170. The term "detection signal," as used herein, may refer to any of the signals generated within front end processing circuitry 150 as it processes the output signal of detector 140. Front end processing circuitry 150 may perform various analog and digital processing of the detector signal. One exemplary detector signal that may be received by front end processing circuitry 150 is shown in FIG. 2B.

Figure 2B:
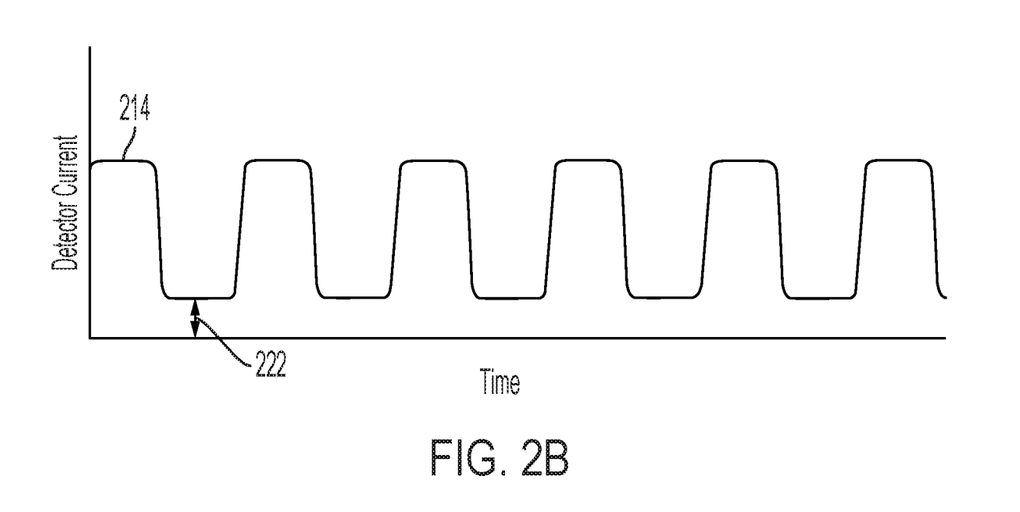
FIG. 2B shows an illustrative plot of a detector signal in accordance with some embodiments of the present disclosure.

FIG. 2B shows an illustrative plot of detector signal 214 that may be generated by a sensor in accordance with some embodiments of the present disclosure. The peaks of detector current waveform 214 may represent current signals provided by a detector, such as detector 140 of FIG. 1, when light is being emitted from a light source. The amplitude of detector current waveform 214 may be proportional to the light incident upon the detector. The peaks of detector current waveform 214 may be synchronous with light drive pulses driving one or more emitters of a light source, such as light source 130 of FIG. 1. For example, detector current waveform 214 may be generated in response to a light source being driven by the light drive signal of FIG. 2A. The valleys of detector current waveform 214 may be synchronous with periods of time during which no light is being emitted by the light source. While no light is being emitted by a light source during the valleys, detector current waveform 214 may not fall all of the way to zero. Rather, dark current 222 may be present in the detector waveform.

As we have noted above, in exemplary embodiments, an analysis of the dark current 222 can provide indication of motion (which may include triboelectric effects, among other motion) and/or external interference. In exemplary embodiments, detection continues during a dark period, with a determination of percent modulation in the dark period to determine a motion signal. In further exemplary embodiments, such dark period motion signal is used to remove motion and/or to warn the system that motion is present (for example as an indicator to ignore non-dark period measurements).

In further exemplary embodiments, the signal detected during the dark period is analyzed to detect external interference (which may otherwise look like a pulse), for example from overhead LED lighting, EMI, surgical equipment, etc. In further exemplary embodiments, such dark period external interference signal is used to remove external interference and/or to warn the system that external interference is present (for example as an indicator to ignore non-dark period measurements).

In exemplary embodiments, since dark current 222 may interfere with accurate determinations of physiological characteristics, dark current 222 may be removed prior to analysis to detect motion and/or external interference, as discussed in more detail below. Further, such detected motion and/or external interference may itself be removed from the non-dark current and/or indicated to the system to improve motion and/or interference tolerance of measurements. In exemplary embodiments, one dark periods or the average of the dark period before and after may be used to detect the presence of motion. In further exemplary embodiments, motion rejection or flagging occurs subsequent such action.

It will be understood that the detector signal shown in FIG. 2B is merely illustrative. In embodiments, the curvature of the waveform may be more varied or complex. In some embodiments, it may be desirable to generate Red and IR peaks in the detector signal that are of similar amplitude (e.g., as shown in FIG. 2B). In some embodiments, it may not be desirable or possible to generate Red and IR peaks in the detector signal that are of similar amplitude. For example, it may be difficult to generate a sufficiently sized Red peak for subjects with dark pigment or with thick fingers. In such a situation, the IR peaks in the detectors signal may be generated with a larger amplitude to facilitate, for example, a heart rate calculation even if it may be difficult to calculate oxygen saturation.

Referring back to FIG. 1, front end processing circuitry 150, which may receive a detection signal, such as detector current waveform 214, may include analog conditioning 152, analog-to-digital converter 154, demultiplexer 156, digital conditioning 158, decimation/interpolator 160, and dark removal 162.

Analog conditioning 152 may perform any suitable analog conditioning of the detector signal. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. In exemplary embodiments, conditioning, decimation or interpolation that is applied to the light "on" signal is also applied to the dark "off" signal. This provides the same aliasing, and the same frequency responses so that motion or interference is the same in the dark "off" period as in the light "on" period.

The conditioned analog signal may be processed by analog-to-digital converter 154, which may convert the conditioned analog signal into a digital signal. Analog-to-digital converter 154 may operate under the control of control circuitry 110. Analog-to-digital converter 154 may use timing control signals from control circuitry 110 to determine when to sample the analog signal. Analog-to-digital converter 154 may be any suitable type of analog-to-digital converter of sufficient resolution to enable a physiological monitor to accurately determine physiological parameters.

Demultiplexer 156 may operate on the analog or digital form of the detector signal to separate out different components of the signal. For example, detector current waveform 214 of FIG. 2B includes a Red component, an IR component, and at least one dark component. Demultiplexer 156 may operate on detector current waveform 214 of FIG. 2B to generate a Red signal, an IR signal, a first dark signal (e.g., corresponding to the dark component that occurs immediately after the Red component), and a second dark signal (e.g., corresponding to the dark component that occurs immediately after the IR component). Demultiplexer 156 may operate under the control of control circuitry 110. For example, demultiplexer 156 may use timing control signals from control circuitry 110 to identify and separate out the different components of the detector signal. In some embodiments, demultiplexer 156 may perform demodulation operations in addition to or in place of demultiplexing operations.

Digital conditioning 158 may perform any suitable digital conditioning of the detector signal. The digital conditioning may include any type of digital filtering of the signal (e.g., low pass, high pass, band pass, notch, or any other suitable filtering), amplifying, performing an operation on the signal, performing any other suitable digital conditioning, or any combination thereof.

The physiological signal may include one or more noise components. The noise components may include the effects of ambient light reaching the detector. Other sources of noise may include 50 or 60 Hz power line noise, subject movement, and/or other non-physiological or undesired physiological signal components. In some circumstances, the noise component can degrade the physiological signal being processed and decrease its signal-to-noise ratio. A low signal-to-noise ratio may make an accurate determination of the physiological parameter difficult.

Accordingly, the physiological signal being analyzed may be processed in order to reduce or remove the noise component. As has been noted above, the dark current signal itself may be analyzed to identify various noise components, including motion and external interference. Additionally, the processing to reduce or remove the noise component may introduce unwanted distortion into the physiological signal. Therefore, the physiological signal may be further processed to reduce or remove the introduced distortion.

Decimator/interpolator 160 may decrease/increase the number of samples in the digital detector signal. For example, decimator/interpolator 160 may decrease the number of samples by removing samples from the detector signal or replacing samples with a smaller number of samples. The decimation or interpolation operation may include or be followed by filtering to smooth the output signal.

Dark removal 162 may be performed on the digital signal. In some embodiments, dark removal 162 may remove dark values from the Red and IR components to generate adjusted Red and IR signals. Additionally, identified motion and/or interference aspects from the dark period may be removed as part of the adjustment.

The components of front end processing circuitry 150 are merely illustrative and any suitable components and combinations of components may be used to perform the front end processing operations.

The front end processing circuitry 150 may be configured to take advantage of the full dynamic range of analog-to-digital converter 154. This may be achieved by applying gain to the detection signal by analog conditioning 152 to map the expected range of the detection signal to the full or close to full output range of analog-to-digital converter 154. The output value of analog-to-digital converter 154, as a function of the total analog gain applied to the detection signal, may be given as:

$$\text{ADC Value} \propto \text{Total Analog Gain} \times [\text{Ambient Light} + \text{LED Light}].$$

Ideally, when ambient light is zero and when the light source is off, the analog-to-digital converter 154 will read just above the minimum input value. When the light source is on, the total analog gain may be set such that the output of analog-to-digital converter 154 may read close to the full scale of analog-to-digital converter 154 without saturating. This may allow the full dynamic range of analog-to-digital converter 154 to be used for representing the detection signal, thereby increasing the resolution of the converted signal. In some embodiments, the total analog gain may be reduced by a small amount so that small changes in the light level incident on the detector do not cause saturation of analog-to-digital converter 154.

However, if the contribution of ambient light is large relative to the contribution of light from a light source, the total analog gain applied to the detection current may need to be reduced to avoid saturating analog-to-digital converter 154. When the analog gain is reduced, the portion of the signal corresponding to the light source may map to a smaller number of analog-to-digital conversion bits. Thus, more ambient light noise in the input of analog-to-digital converter 154 may results in fewer bits of resolution for the portion of the signal from the light source. This may have a detrimental effect on the signal-to-noise ratio of the detection signal. Therefore, it may be desirable to reduce the effect of ambient light on the detection signal that is applied to analog-to-digital converter 158, and thereby reduce the contribution of the noise component to the converted digital signal. In exemplary embodiments, an offset current is utilized to counteract contribution of the noise component to the converted digital signal, e.g., utilizing methods of percent modulation calculation for known offset values.

Back end processing circuitry 170 may include processor 172 and memory 174. Processor 172 may be adapted to execute software, which may include an operating system and one or more applications, as part of performing the functions described herein. Processor 172 may receive and further physiological signals received from front end processing circuitry 150. For example, processor 172 may determine one or more physiological parameters based on the received physiological signals. Memory 174 may include any suitable computer-readable media capable of storing information that can be interpreted by processor 172. This information may be data or may take the form of computer-executable instructions, such as software applications, that cause the microprocessor to perform certain functions and/or computer-implemented methods, Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system. Back end processing circuitry 170 may be communicatively coupled with use interface 180 and communication interface 190.

User interface 180 may include user input 182, display 184, and speaker 186. User input 182 may include any type of user input device such as a keyboard, a mouse, a touch screen, buttons, switches, a microphone, a joy stick, a touch pad, or any other suitable input device. The inputs received by user input 182 can include information about the subject, such as age, weight, height, diagnosis, medications, treatments, and so forth. In an embodiment, the subject may be a medical patient and display 184 may exhibit a list of values which may generally apply to the patient, such as, for example, age ranges or medication families, which the user may select using user inputs 182. Additionally, display 184 may display, for example, an estimate of a subject's blood oxygen saturation generated by monitor 104 (referred to as an "SpO2" measurement), pulse rate information, respiration rate information, blood pressure, any other parameters, and any combination thereof Display 184 may include any type of display such as a cathode ray tube display, a flat panel display such a liquid crystal display or plasma display, or any other suitable display device. Speaker 186 within user interface 180 may provide an audible sound that may be used in various embodiments, such as for example, sounding an audible alarm in the event that a patient's physiological parameters are not within a predefined normal range.

Communication interface 190 may enable monitor 104 to exchange information with external devices. Communications interface 190 may include any suitable hardware, software, or both, which may allow monitor 104 to communicate with electronic circuitry, a device, a network, a server or other workstations, a display, or any combination thereof. Communications interface 190 may include one or more receivers, transmitters, transceivers, antennas, plug-in connectors, ports, communications buses, communications protocols, device identification protocols, any other suitable hardware or software, or any combination thereof. Communications interface 190 may be configured to allow wired communication (e.g., using USB, RS-232 or other standards), wireless communication (e.g., using WiFi, IR, WiMax, BLUETOOTH, UWB, or other standards), or both. For example, communications interface 190 may be configured using a universal serial bus (USB) protocol (e.g., USB 2.0, USB 3.0), and may be configured to couple to other devices (e.g., remote memory devices storing templates) using a four-pin USB standard Type-A connector (e.g., plug and/or socket) and cable. In some embodiments, communications interface 190 may include an internal bus such as, for example, one or more slots for insertion of expansion cards.

It will be understood that the components of physiological monitoring system 100 that are shown and described as separate components are shown and described as such for illustrative purposes only. In some embodiments the functionality of some of the components may be combined in a single component. For example, the functionality of front end processing circuitry 150 and back end processing circuitry 170 may be combined in a single processor system. Additionally, in some embodiments the functionality of some of the components of monitor 104 shown and described herein may be divided over multiple components. For example, some or all of the functionality of control circuitry 110 may be performed in front end processing circuitry 150, in back end processing circuitry 170, or both. In other embodiments, the functionality of one or more of the components may be performed in a different order or may not be required. In an embodiment, all of the components of physiological monitoring system 100 can be realized in processor circuitry.

Figure 3:
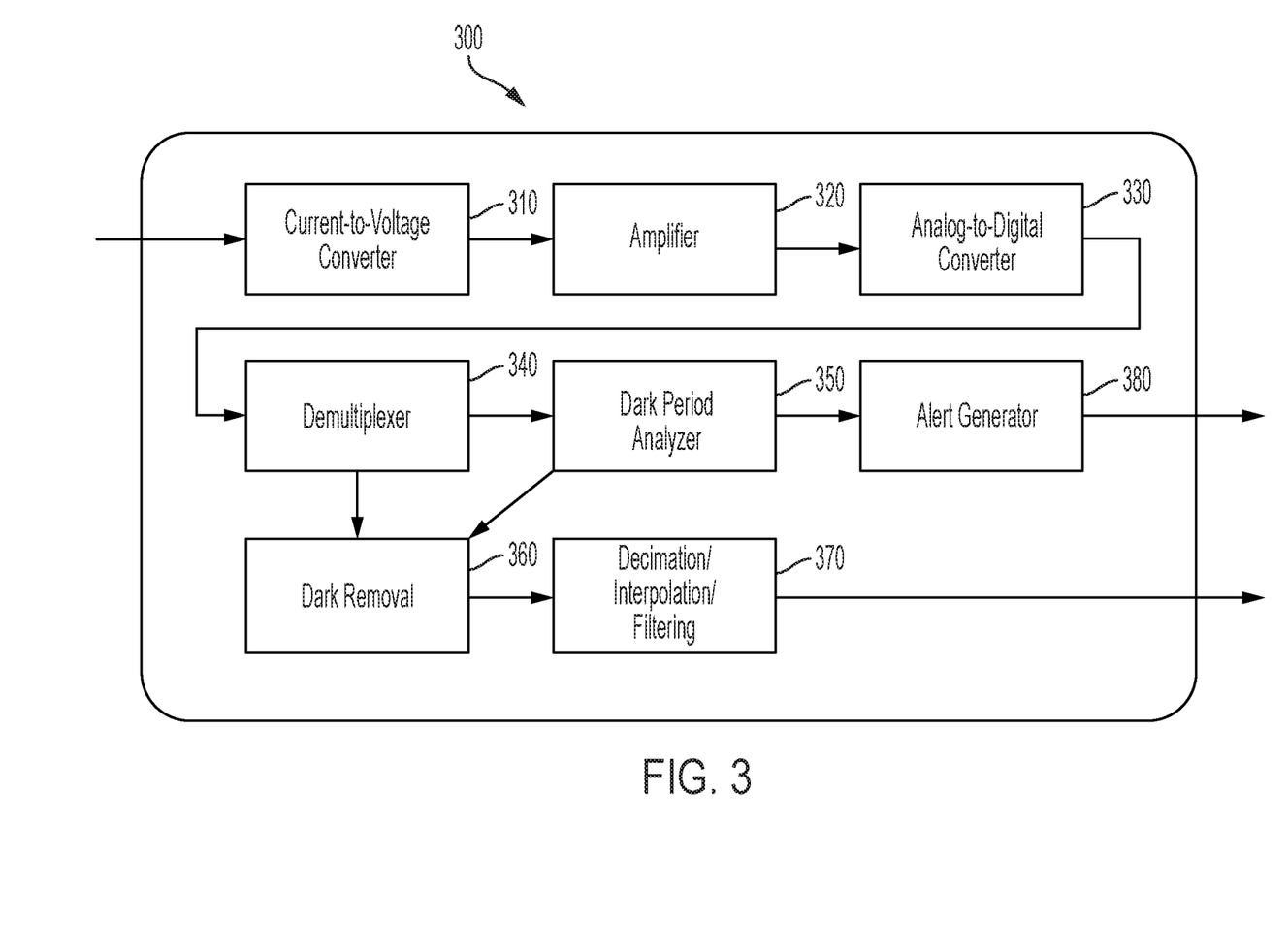
FIG. 3 shows a block diagram of illustrative front end circuitry in accordance with some embodiments of the present disclosure.

FIG. 3 shows a block diagram of illustrative front end processing circuitry 300 in accordance with some embodiments of the present disclosure for receiving and processing signals from a sensor device. In some embodiments, front end processing circuitry 300 may be included in a physiological monitoring system such as system 100 of FIG. 1. In such embodiments, front end processing circuitry 300 may receive and process signals from sensor 102 of FIG. 1. Front end processor circuitry 300 may include current-to-voltage converter 310 which may convert a current signal into a voltage signal. For example, current-to-voltage converter 310 may receive and convert a detector current waveform such as detector current waveform 214 of FIG. 2B. Front end processing circuitry 300 may also include an amplifier 320 and analog-to-digital converter 330. The detection signal in front end processing circuitry 300 may also demultiplexed by demultiplexer 340 (It will be understood that demultiplexing of the detection signal can be performed in the analog domain or the digital domain). Dark removal 360 and decimation/interpolation/filtering 370 may also be included within front end processing circuitry 300.

As we have noted, a dark period analyzer 350 may be used to provide interference and motion detection during the dark period. Where additional dark removal 360 is desired, information from the dark period analyzer 350 may be provided to the dark removal module 360. Additionally, or in the alternative, the dark period analyzer 350 may provide information to an alert generator 380 to provide relevant alerts, e.g., to warn the system that motion is present, etc.

In an embodiment, the components of front end processing circuitry 300 that are shown and described may be implemented in a single processor system. In other embodiments the functionality of some of the components may be implemented in separate components. For example, the functionality of some or all of the components may be implemented in back end processing circuitry or in other processor circuitry. In other embodiments, the functionality of one or more of the components may not be required. In some embodiments, components 310, 320, and 330 may all be analog conditioning components that may be in implemented as part of analog conditioning 152 of FIG. 1. In some embodiments, components 340, 360, and 365 may be implemented as part of analog-to-digital converter 154, demultiplexer 156, and dark removal 162 of FIG. 1, respectively, and include the functionality of these components as described above. In some embodiments, decimation/interpolation/filtering 370 may be implemented as part of digital conditioning 158 and decimator/interpolator 160 of FIG. 1 and include the functionality of these components as described above. In some embodiments, an anti-aliasing filter (e.g., a low pass filter) may be included in front end processing circuitry 300. The anti-aliasing filter may be included, for example, as part of amplifier 320 or between amplifier 320 and analog-to-digital converter 330.

Front end processing circuitry 300 may receive a detection signal such as detector current waveform 214 of FIG. 2B when light from a light source is incident on a detector, which converts the intensity of the received light into an electrical detection signal. The amplitude of the detection signal may be proportional to the light incident upon the detector. Since the detection signal from the detector may be a small current signal, it may be converted to a voltage signal and amplified before being converted to a digital signal. Accordingly, in some embodiments, current-to-voltage converter 310 may receive the detection signal from the detector and convert the detection signal from a current detection signal to a voltage detection signal.

Ambient light incident on the detector such as detector 140 of FIG. 1 may be at a relatively low frequency. The light source, such as light source 130 of FIG. 1, may be modulated at a relatively high frequency. For example, the repetition rate for the drive cycle, such as the drive cycle shown in FIG. 2A, may be 625 Hz, 1211 Hz, 311 Hz, or any other suitable frequency. In some applications, it may be possible for a high pass filter (not shown) to substantially pass the peaks of the detection signal such as detector current waveform 214 of FIG. 2B while stripping away or substantially attenuating the ambient light or dark component before it reaches the analog-to-digital converter. Depending on the cutoff frequency of a high pass filter, a high pass filter may also reject other noise in the detection signal such as the lower harmonics of AC line noise or fluorescent lighting. Some exemplary embodiments herein contemplate the lack of a high pass filter in order to better measure the signal during dark periods, therefore gaining a better picture of interference and motion detection during those dark periods. Other exemplary embodiments contemplate use of a high pass filter, where DC signals before the filter are measured and retained (either digitally or with the physical signal).

As we have noted, dark removal may then be performed on the detection signal by dark removal 360. In dark removal 365, a removal amount is determined from the dark signal portion of the detection signal and removed from the peak portion of the detection signal in order to reduce the effect of dark signal on the peak. For example, in reference to FIG. 2A, a detection signal peak corresponding to Red light drive pulse 202 may be adjusted by determining the amount of dark signal during the dark period 220 preceding Red light drive pulse 202. The dark signal amount determined in this manner may be removed from the detector peak corresponding to Red light drive pulse 202. Alternatively, the dark period 220 after Red light drive pulse 202 may be used to correct Red light drive pulse 202 rather than the dark period 220 preceding it. Additionally, an average of the dark periods 220 before and after Red light drive pulse 202 may be used. It will be understood that the dark removal need not be performed on the detection signal immediately after demultiplexing, and that it may be performed at any other suitable point within front end processing circuitry 300.

Exemplary methods for motion rejection include utilizing a motion signal to remove a similar signal from the PPG signal, e.g., via: simple subtraction; a scaled subtraction; assessment of the frequency content of the noise with creation of a filter to remove such noise; addition of an inverted signal to cancel noise in the PPG signal; use of an adaptive filter; use of least means square methods, or the like.

Additionally, exemplary methods for flagging motion or interference, e.g., via alert generator 380 to provide relevant alerts to warn the system that motion is present, includes use of a threshold, use of an integrated threshold, assessment of frequency content to determine whether to generate a flag or alert, or combinations thereof.

In view of the foregoing, the present disclosure provides techniques for processing a physiological signal such as a detection signal. The detection signal may be received from a detector and include noise such as ambient light noise. The detection signal may be analyzed during the dark period in order to better determine the existence of interference and motion effects present in the signal.

Physiological parameters may then be accurately calculated based upon the processed detection signal. The physiological parameters that can be calculated may include, for example, pulse rate, respiration rate, blood oxygen saturation, blood pressure, any other suitable parameters, or any combination thereof. These physiological parameters can be calculated using any known calculation techniques.

Figure 4:
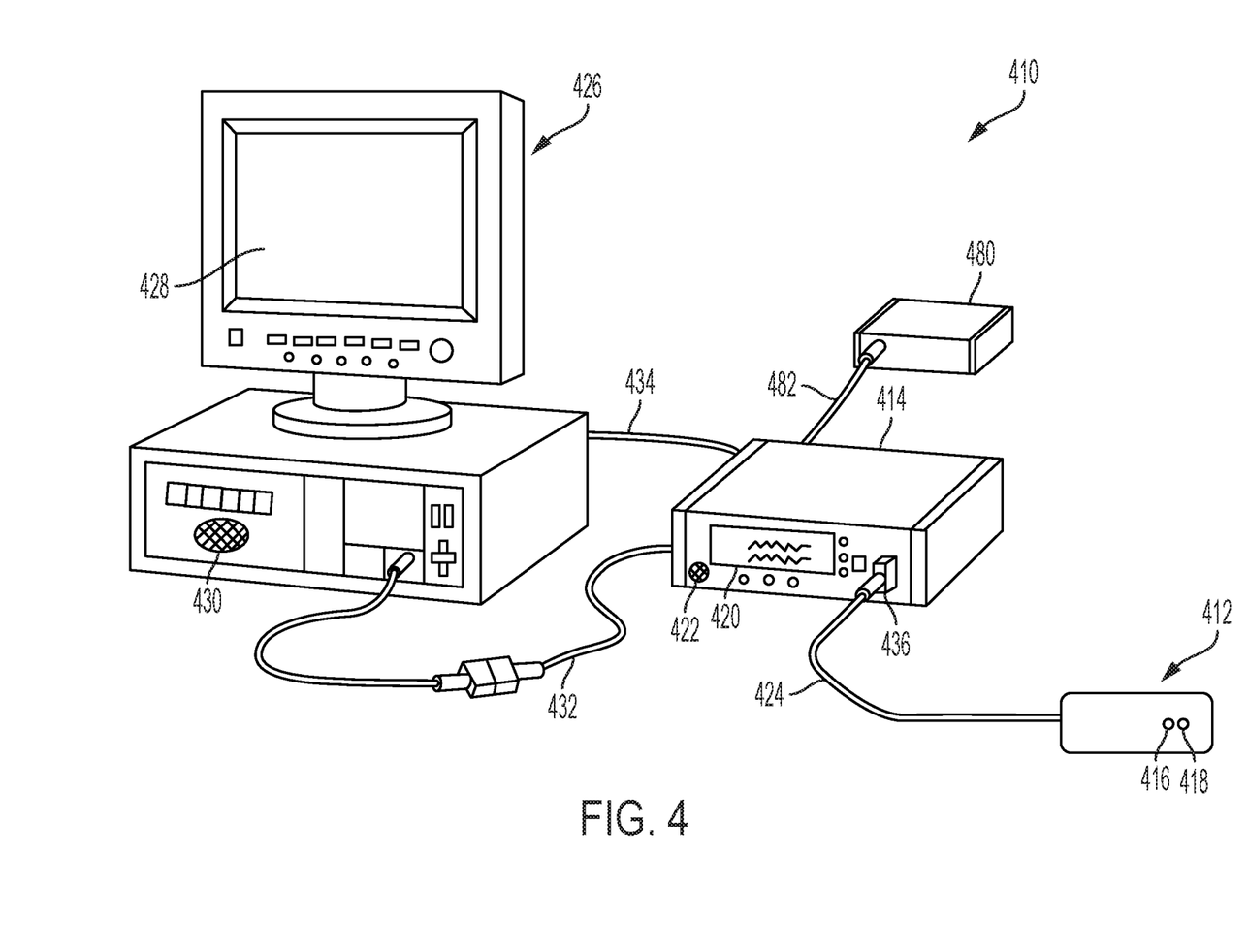
FIG. 4 shows an illustrative physiological monitoring system in accordance with some embodiments of the present disclosure.

FIG. 4 is a perspective view of an embodiment of physiological monitoring system 410. In some embodiments, one or more components of physiological monitoring system 410 may include the front end processing of the present disclosure. For example, physiological monitoring system 410 may include front end processing circuitry 300 of FIG. 3 or one or more components of physiological monitoring system 100 of FIG. 1.

Physiological monitoring system 410 may include a monitor 414 which may be coupled to sensor unit 412. In some embodiments, sensor unit 412 may be part of an oximeter. Additionally, monitor 414 may be wirelessly coupled (not shown) to sensor unit 412. Sensor unit 412 may include light source 416 for emitting light at one or more wavelengths into a subject's tissue. Detector 418 may also be provided in sensor unit 412 for detecting the light originally from light source 416 that emanates from the subject's tissue after passing through the tissue. Any suitable physical configuration of light source 416 and detector 418 may be used. In an embodiment, sensor unit 412 may include multiple emitters and/or detectors, which may be spaced apart. Physiological monitoring system 410 may also include one or more additional sensor units (not shown) which may take the form of any of the embodiments described herein with reference to sensor 102 or sensor unit 412. An additional sensor unit may be the same type of sensor unit as sensor unit 412, or a different sensor unit type than sensor unit 412.

Calibration device 480, which may be powered by monitor 414, a battery, or by a conventional power source such as a wall outlet, may include any suitable calibration device. Calibration device 480 may be communicatively coupled to monitor 414 via communicative coupling 482, and/or may communicate wirelessly (not shown). In some embodiments, calibration device 480 is completely integrated within monitor 414. In some embodiments, calibration device 480 may include a manual input device (not shown) used by an operator to manually input reference signal measurements obtained from some other source (e.g., an external invasive or non-invasive physiological measurement system).

Multiple sensor units may be capable of being positioned at two different locations on a subject's body; for example, a first sensor unit may be positioned on a subject's forehead, while a second sensor unit may be positioned at a subject's fingertip. Sensor units may each detect any signal that carries information about a subject's physiological state, such as arterial line measurements or the pulsatile force exerted on the walls of an artery using, for example, oscillometric methods with a piezoelectric transducer. According to another embodiment, system 410 may include a plurality of sensors forming a sensor array in lieu of either or both of the sensor units. Each of the sensors of a sensor array may be a complementary metal oxide semiconductor (CMOS) sensor. Alternatively, each sensor of an array may be a charged coupled device (CCD) sensor. In some embodiments, a sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier. It will be understood that any type of sensor, including any type of physiological sensor, may be used in one or more sensor units in accordance with the systems and techniques disclosed herein. It is understood that any number of sensors measuring any number of physiological signals may be used to determine physiological information in accordance with the techniques described herein.

In some embodiments, light source 416 and detector 418 may be on opposite sides of a digit such as a finger or toe, in which case the light that is emanating from the tissue has passed completely through the digit. In an embodiment, light source 416 and detector 418 may be arranged so that light from light source 416 penetrates the tissue and is reflected by the tissue into detector 418, such as in a sensor designed to obtain pulse oximetry data from a subject's forehead.

In some embodiments, a sensor may be connected to and draw its power from monitor 414. In another embodiment, a sensor wirelessly connected to monitor 414 may include its own battery or similar power supply (not shown). Monitor 414 may be configured to calculate physiological parameters (e.g., pulse rate, blood pressure, blood oxygen saturation) based at least in part on data relating to light emission and detection received from one or more sensor units such as sensor unit 412. In an alternative embodiment, the calculations may be performed on the sensor units or an intermediate device and the result of the calculations may be passed to monitor 414. Further, monitor 414 may include a display 420 configured to display the physiological parameters or other information about the system. In the embodiment shown, monitor 414 may also include a speaker 422 to provide an audible sound that may be used in various other embodiments, such as for example, sounding an audible alarm in the event that a subject's physiological parameters are not within a predefined normal range. In some embodiments, the monitor 414 includes a blood pressure monitor. In some embodiments, the system 410 includes a stand-alone blood pressure monitor in communication with the monitor 414 via a cable or a wireless network link. In an embodiment, a sensor such as sensor unit 412 may be communicatively coupled to monitor 414 via cable connection port 436. The cable connection may be used instead of or in addition to a wireless connection.

In the illustrated embodiment, system 410 includes a multi-parameter physiological monitor 426. The monitor 426 may include a cathode ray tube display, a flat panel display (as shown) such as a liquid crystal display (LCD) or a plasma display, or may include any other type of monitor now known or later developed. Multi-parameter physiological monitor 426 may be configured to calculate physiological parameters and to provide a display 428 for information from monitor 414 and from other medical monitoring devices or systems (not shown). For example, multi-parameter physiological monitor 426 may be configured to display pulse rate information from monitor 414, an estimate of a subject's blood oxygen saturation generated by monitor 414 (referred to as an "SpO2" measurement), and blood pressure from monitor 414 on display 428. Multi-parameter physiological monitor 426 may include a speaker 430.

Monitor 414 may be communicatively coupled to multi-parameter physiological monitor 426 via a cable 432 or 434 or a digital communications port, respectively and/or may communicate wirelessly. In addition, monitor 414 and/or multi-parameter physiological monitor 426 may be coupled to a network to enable the sharing of information with servers or other workstations (not shown). Monitor 414 may be powered by a battery (not shown) or by a conventional power source such as a wall outlet.

Figure 5:
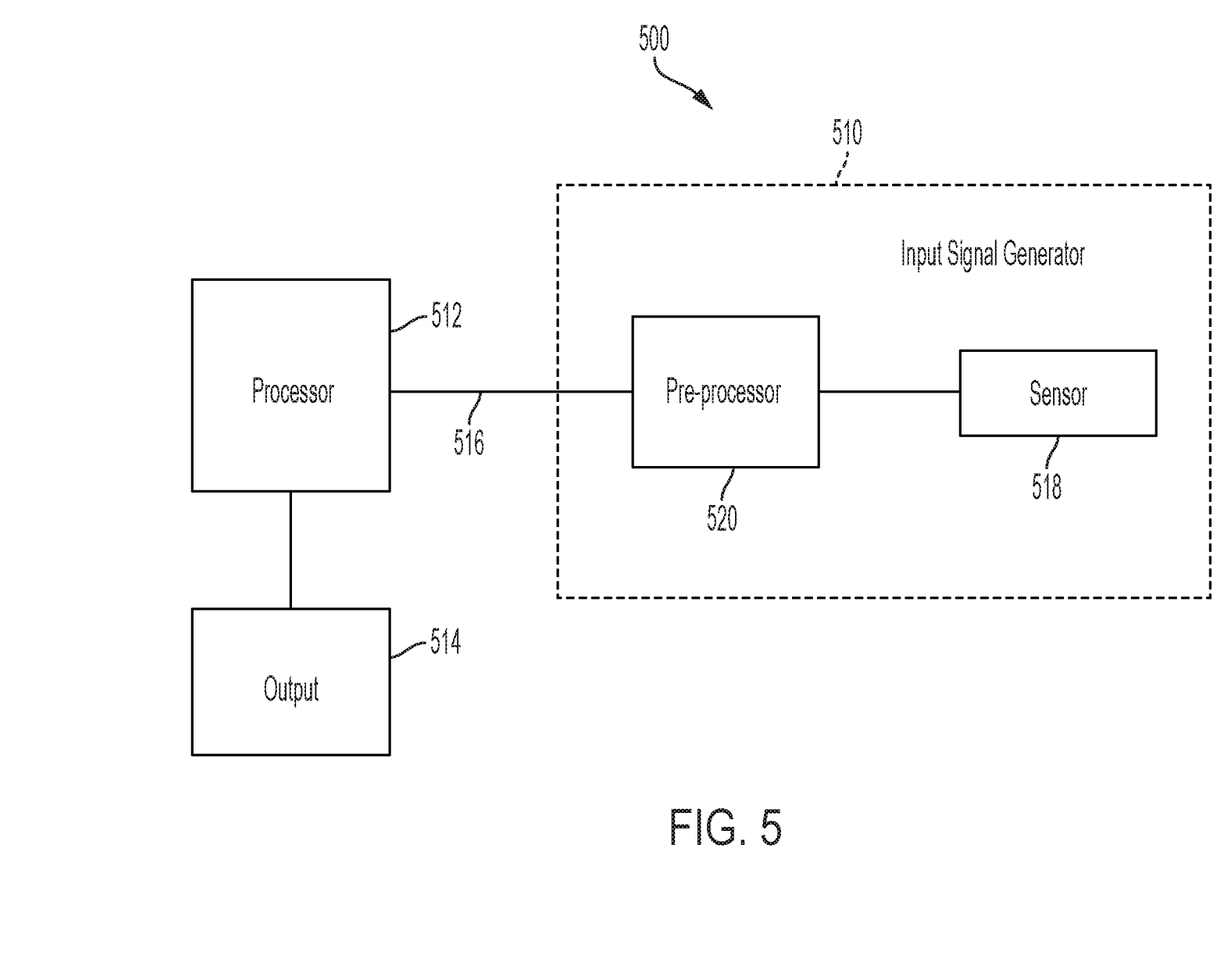
FIG. 5 shows a block diagram of an illustrative signal processing system in accordance with some embodiments of the present disclosure.

FIG. 5 is an illustrative signal processing system 500 in accordance with an embodiment that may implement the signal processing techniques described herein. Signal processing system 500 includes input signal generator 510, processor 512 and output 514. In the illustrated embodiment, input signal generator 510 may include pre-processor 520 coupled to sensor 518. As illustrated, input signal generator 510 generates an input signal 516. In some embodiments, input signal 516 may include one or more intensity signals based on a detector output. In some embodiments, pre-processor 520 may be an oximeter and input signal 516 may be a PPG signal. In an embodiment, pre-processor 520 may be any suitable signal processing device and input signal 516 may include PPG signals and one or more other physiological signals. It will be understood that input signal generator 510 may include any suitable signal source, signal generating data, signal generating equipment, or any combination thereof to produce signal 516. Signal 516 may be a single signal, or may be multiple signals transmitted over a single pathway or multiple pathways.

Pre-processor 520 may apply one or more signal processing operations to the signal generated by sensor 518. For example, pre-processor 520 may apply a pre-determined set of processing operations to the signal provided by sensor 518 to produce input signal 516 that can be appropriately interpreted by processor 512, such as performing A/D conversion. In some embodiments, A/D conversion may be performed by processor 512. Pre-processor 520 may also perform any of the following operations on the signal provided by sensor 518: reshaping the signal for transmission, multiplexing the signal, modulating the signal onto carrier signals, compressing the signal, encoding the signal, and filtering the signal. In some embodiments, pre-processor 520 may include a current-to-voltage converter (e.g., to convert a photocurrent into a voltage), an amplifier, a filter, and A/D converter, a de-multiplexer, any other suitable pre-processing components, or any combination thereof. In some embodiments, pre-processor 520 may include one or more components from front end processing circuitry 300 of FIG. 3.

In some embodiments, signal 516 may include PPG signals corresponding to one or more light frequencies, such as an IR PPG signal and a Red PPG signal. In some embodiments, signal 516 may include signals measured at one or more sites on a subject's body, for example, a subject's finger, toe, ear, arm, or any other body site. In some embodiments, signal 516 may include multiple types of signals (e.g., one or more of an ECG signal, an EEG signal, an acoustic signal, an optical signal, a signal representing a blood pressure, and a signal representing a heart rate). Signal 516 may be any suitable biosignal or any other suitable signal.

In some embodiments, signal 516 may be coupled to processor 512. Processor 512 may be any suitable software, firmware, hardware, or combination thereof for processing signal 516. For example, processor 512 may include one or more hardware processors (e.g., integrated circuits), one or more software modules, computer-readable media such as memory, firmware, or any combination thereof. Processor 512 may, for example, be a computer or may be one or more chips (i.e., integrated circuits). Processor 512 may, for example, include an assembly of analog electronic components. Processor 512 may calculate physiological information. For example, processor 512 may compute one or more of a pulse rate, respiration rate, blood pressure, or any other suitable physiological parameter. Processor 512 may perform any suitable signal processing of signal 516 to filter signal 516, such as any suitable band-pass filtering, adaptive filtering, closed-loop filtering, any other suitable filtering, and/or any combination thereof. Processor 512 may also receive input signals from additional sources (not shown). For example, processor 512 may receive an input signal containing information about treatments provided to the subject. Additional input signals may be used by processor 512 in any of the calculations or operations it performs in accordance with processing system 500.

In some embodiments, all or some of pre-processor 520, processor 512, or both, may be referred to collectively as processing equipment. In some embodiments, any of the processing components and/or circuits, or portions thereof, of FIGS. 1, 3, 4, and 5 may be referred to collectively as processing equipment. For example, processing equipment may be configured to amplify, filter, sample and digitize input signal 516 (e.g., using an analog-to-digital converter), and calculate physiological information from the digitized signal. In some embodiments, all or some of the components of the processing equipment may be referred to as a processing module.

Processor 512 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 512 to, for example, store fiducial information or initialization information corresponding to physiological monitoring. In some embodiments, processor 512 may store physiological measurements or previously received data from signal 516 in a memory device for later retrieval. In some embodiments, processor 512 may store calculated values, such as a pulse rate, a blood pressure, a blood oxygen saturation, a fiducial point location or characteristic, an initialization parameter, or any other calculated values, in a memory device for later retrieval.

Processor 512 may be coupled to output 514. Output 514 may be any suitable output device such as a serial port which can interface with many types of devices, or another interface with one or more medical devices (e.g., a medical monitor that displays various physiological parameters, a medical alarm, or any other suitable medical device that either displays physiological parameters or uses the output of processor 512 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 500 may be incorporated into system 100 of FIG. 1 in which, for example, input signal generator 510 may be implemented as part of sensor 102, or into system 410 of FIG. 4 in which, for example, input signal generator 510 may be implemented as part of sensor unit 412 (FIG. 4), and processor 512 may be implemented as part of monitor 104 (FIG. 1) or as part of monitor 414 (FIG. 4). Furthermore, all or part of system 500 may be embedded in a small, compact object carried with or attached to the subject (e.g., a watch, other piece of jewelry, or a smart phone). In some embodiments, a wireless transceiver (not shown) may also be included in system 500 to enable wireless communication with other components of systems 100 and 410 (FIGS. 1 and 4). As such, systems 100 and 410 may be part of a fully portable and continuous subject monitoring solution. In some embodiments, a wireless transceiver (not shown) may also be included in system 500 to enable wireless communication with other components of systems 100 and 410 (FIGS. 1 and 4). For example, pre-processor 520 may output signal 516 over BLUETOOTH, 802.11, WiFi, WiMax, cable, satellite, Infrared, or any other suitable transmission scheme. In some embodiments, a wireless transmission scheme may be used between any communicating components of system 500. In some embodiments, system 500 may include one or more communicatively coupled modules configured to perform particular tasks. In some embodiments, system 500 may be included as a module communicatively coupled to one or more other modules.

It will be understood that the components of signal processing system 500 that are shown and described as separate components are shown and described as such for illustrative purposes only. In other embodiments the functionality of some of the components may be combined in a single component. For example, the functionality of processor 512 and pre-processor 520 may combined in a single processor system. Additionally, the functionality of some of the components shown and described herein may be divided over multiple components. Additionally, signal processing system 500 may perform the functionality of other components not show in FIG. 5. For example, some or all of the functionality of control circuitry 110 of FIG. 1 may be performed in signal processing system 500. In other embodiments, the functionality of one or more of the components may not be required. In an embodiment, all of the components can be realized in processor circuitry.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of processing a physiological signal to determine a physiological parameter of a subject, the method comprising:

receiving a signal using a photoplethysmography system, wherein the signal comprises a first component, attenuated by a subject, measured during an light-on period and a second component measured during a light-off period;

performing a first analysis operation on the signal from said second component to identify interference or motion artifacts, wherein a DC portion of the light-off period is permitted to pass through during the first analysis operation and wherein said analysis operation assesses the percent modulation of the LED-off period; and determining the physiological parameter based on the signal.

2. The method of claim 1, wherein the light-off period corresponds to an LED-off period that is unfiltered by high pass filtering.

3. The method of claim 1, further comprising removing detected interference or motion artifacts from the light signal of the first component.

4. The method of claim 1, further comprising generating an alert signal representative of interference.

5. The method of claim 1, further comprising generating an alert signal representative of motion.

6. The method of claim 1, further comprising generating a photonic signal comprising at least one wavelength of light, wherein the desired component of the detected light signal corresponds to the photonic signal, wherein the photonic signal comprises a plurality of first segments and a plurality of second segments, wherein light is transmitted during the first segments and no light is transmitted during the second segments, and wherein the first segments and the second segments alternate.

7. The method of claim 1, wherein the physiological parameter comprises one or more of a pulse rate, a respiration rate, and a blood oxygen saturation of the subject.

8. The method of claim 1, wherein the photoplethysmography system includes a pulse oximeter.

9. A photoplethysmography system for processing a physiological signal to determine a physiological parameter of a subject, the system comprising:

a photoplethysmography sensor configured to receive a signal attenuated by a subject, wherein the signal comprises a first component measured during a light-on period and a second component measured during a light-off period, wherein the photoplethysmography system comprises:

a first dark period analysis module configured to perform an analysis operation on the signal from said second component to identify interference or motion artifacts, wherein a DC portion of the dark period is permitted to pass through during measurement during the light-off period and wherein said analysis operation assesses the percent modulation of the LED-off period; and a processor configured to determine the physiological parameter based on a filtered digital signal.

10. The system of claim 9, further comprising a light source configured to generate a photonic signal comprising at least one wavelength of light, wherein the desired component of the detected light signal corresponds to the photonic signal, wherein the photonic signal comprises a plurality of first segments and a plurality of second segments, wherein light is transmitted during the first segments and no light is transmitted during the second segments, and wherein the first segments and second segments alternate.

11. The system of claim 9, wherein the light-off period corresponds to an LED-off period that is unfiltered by high pass filtering.

12. The system of claim 9, wherein the processor is configured to remove detected interference or motion artifacts from the light signal of the first component.

13. The system of claim 9, wherein the processor is configured to generate an alert signal representative of interference.

14. The system of claim 9, wherein the processor is configured to generate an alert signal representative of motion.

15. The system of claim 9, wherein the physiological parameter comprises one or more of a pulse rate, a respiration rate, and a blood oxygen saturation of the subject.

16. The system of claim 9, wherein the photoplethysmography system includes a pulse oximeter.

* * * * *